(12) United States Patent
Ma et al.

(10) Patent No.: US 11,759,451 B2
(45) Date of Patent: Sep. 19, 2023

(54) THERAPEUTIC POTENTIAL OF GLYCOPYRROLATE AND MEXILETINE FOR NERVOUS SYSTEM INJURY

(71) Applicant: City University of Hong Kong, Hong Kong (CN)

(72) Inventors: Chi Him Eddie Ma, Hong Kong (CN); Ngan Pan Bennett Au, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 115 days.

(21) Appl. No.: 17/447,700

(22) Filed: Sep. 15, 2021

(65) Prior Publication Data

US 2022/0079918 A1  Mar. 17, 2022

Related U.S. Application Data

(60) Provisional application No. 63/078,395, filed on Sep. 15, 2020.

(51) Int. Cl.
*A61K 31/40* (2006.01)
*A61P 25/28* (2006.01)
*A61K 31/138* (2006.01)

(52) U.S. Cl.
CPC ............ *A61K 31/40* (2013.01); *A61K 31/138* (2013.01); *A61P 25/28* (2018.01)

(58) Field of Classification Search
CPC ........ A61K 31/40; A61K 31/138; A61P 25/28
See application file for complete search history.

(56) References Cited

U.S. PATENT DOCUMENTS

| | | |
|---|---|---|
| 8,097,633 B2 | 1/2012 | Rich |
| 9,084,753 B2 | 7/2015 | Rich |
| 9,561,218 B2 | 2/2017 | Clarence-Smith et al. |

FOREIGN PATENT DOCUMENTS

| | | |
|---|---|---|
| WO | 99/52522 A1 | 10/1999 |
| WO | 2009/002935 A1 | 12/2008 |

OTHER PUBLICATIONS

P. K. Stys et al. (Neuroscience vol. 71, No. 1, pp. 27-36, 1996.*

* cited by examiner

*Primary Examiner* — Kamal A Saeed
(74) *Attorney, Agent, or Firm* — S&F/WEHRW

(57) ABSTRACT

Provided herein are methods of treating a nervous system injury, such as a central nervous system injury and/or a peripheral nervous system injury, and methods for treating an injured neuron using glycopyrrolate, mexiletine, or a mixture thereof.

16 Claims, 7 Drawing Sheets

THERAPEUTIC POTENTIAL OF GLYCOPYRROLATE AND MEXILETINE FOR NERVOUS SYSTEM INJURY

CROSS-REFERENCE TO RELATED APPLICATIONS

Figure 1:
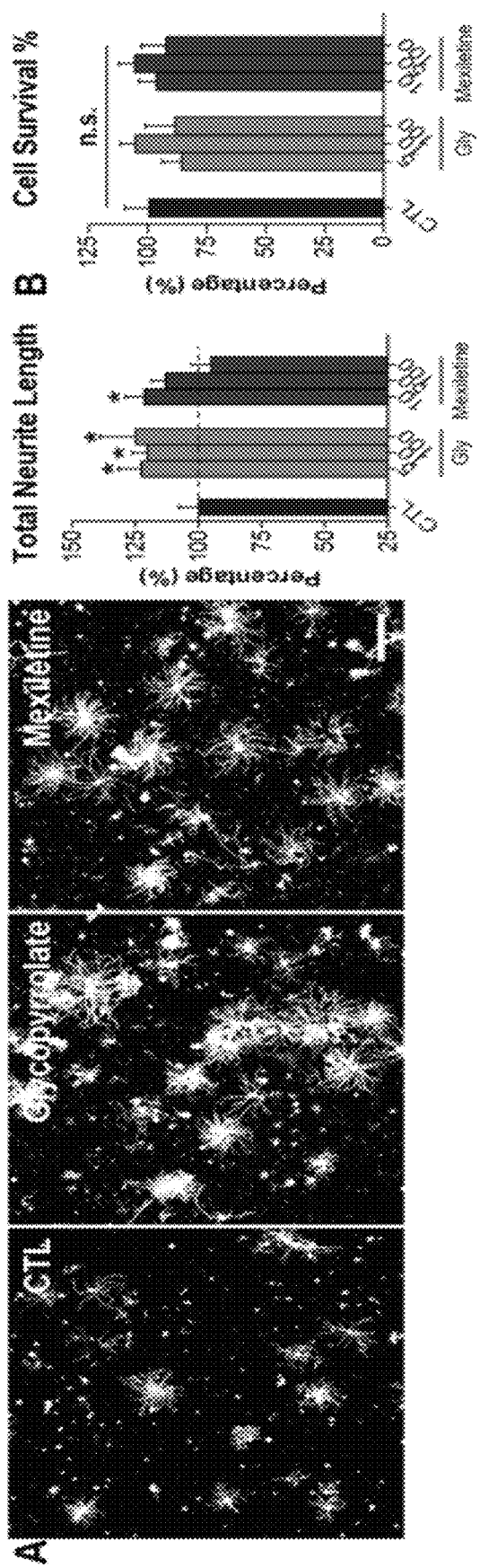

This application claims priority from U.S. Provisional Patent Application No. 63/078,395 filed on Sep. 15, 2020, the content of which is hereby incorporated by reference in its entirety.

TECHNICAL FIELD

The present disclosure relates to method for treating nervous system injuries in a subject in need thereof and methods of promoting neuron growth, regrowth, and repair.

BACKGROUND

Injuries to the nervous system are often devastating to the patients leading to permanent and irreversible loss of their sensory and motor functions. The mature neurons in the central nervous system (CNS) fail to elongate their injured axons across the lesion for target reinnervation largely due to the limited intrinsic regenerative capacity of the neurons. In contrast to CNS neurons, peripheral axons can regenerate at a slow rate (1-2 mm/days) after injury. Although long-distance axon regeneration is feasible after peripheral nerve injury (PNI), chronic denervation prevents the reformation of functional synapses at the motor end plate, resulting in incomplete motor functional recovery.

Currently, there is no effective drug to treat patients suffering from nervous system injuries. Surgical intervention to repair the injured peripheral nerves of the patients immediately after injuries often resulted in minimal clinical meaningful motor functional recovery, largely due to the slow rate of axon regeneration leading to the failure of reformation of functional synapses at the distal targets (i.e. neuromuscular junctions). There is accumulating evidence demonstrating that accelerating the axonal regrowth can promote sensory and motor functional recovery after PNI.

There is thus a need for improved methods for treating nervous system injuries.

SUMMARY

In a first aspect, provided herein is a method of treating a nervous system injury in a subject in need thereof, the method comprising: administering a therapeutically effective amount of a compound selected from the group consisting of a compound of Formula I, a compound of Formula II, and a mixture thereof to the subject, wherein the compound of Formula I has the structure:

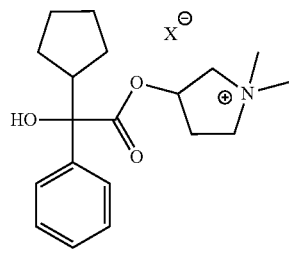

I or a solvate thereof, wherein X is a pharmaceutically acceptable anion; and the compound of Formula II has the structure:

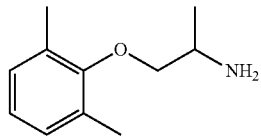

II or a pharmaceutically acceptable salt thereof or a solvate thereof.

In certain embodiments, X is bromide.

In certain embodiments, the nervous system injury is selected from the group consisting of a central nervous system injury and a peripheral nervous system injury.

In certain embodiments, treatment of the nervous system injury results in the regrowth of injured axons.

In certain embodiments, the injured axons comprise neurons.

In certain embodiments, the nervous system injury comprises a peripheral nerve injury.

In certain embodiments, the nervous system injury comprises an optic nerve injury.

In certain embodiments, the compound is administered to the subject by at least one route selected from the group consisting of intravitreally, intraperitoneally, suprachoroidally, subconjunctivally, retrobulbarly, intracamerally, and subretinally.

In certain embodiments, the compound is administered to the subject by at least one route selected from the group consisting of intravitreally, intraperitoneally, and intrathecally.

In certain embodiments, the compound is administered to the subject intraperitoneally.

In certain embodiments, the compound is administered to the subject intravitreally and intraperitoneally at a dosage sufficient to induce axon regeneration in the subject.

In certain embodiments, the compound of Formula I and the compound of Formula II are administered to the subject.

In certain embodiments, the compound is administered to the subject at a dosage of about 0.1 mg/kg to about 100 mg/kg.

In certain embodiments, the compound is administered in a pharmaceutical composition comprising the compound at a concentration of about 0.1 µg/µl to about 20 µg/µl.

In certain embodiments, the compound has Formula I, X is bromide, and the compound is administered to the subject by at least one route selected from the group consisting of intravitreally, intraperitoneally, suprachoroidally, subconjunctivally, retrobulbarly, intracamerally, and subretinally.

In certain embodiments, the compound has Formula II and the compound is administered to the subject by at least one route selected from the group consisting of intravitreally, intraperitoneally, suprachoroidally, subconjunctivally, retrobulbarly, intracamerally, and subretinally.

In a second aspect, provided herein is a method of treating an injured neuron, the method comprising contacting the injured neuron with a compound selected from the group consisting of a compound of Formula I, a compound of Formula II, and a mixture thereof, wherein the compound of Formula I has the structure:

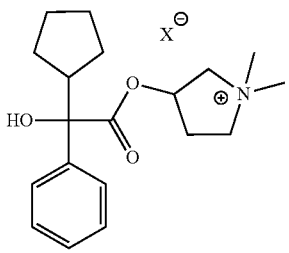

or a solvate thereof, wherein X is a pharmaceutically acceptable anion; and the compound of Formula II has the structure:

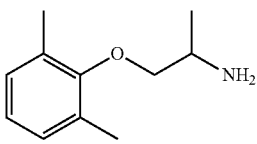

or a pharmaceutically acceptable salt thereof or a solvate thereof, wherein the step of contacting the injured neuron occurs in vitro or ex vivo.

In certain embodiments, the injured neuronal was injured as a result of an optic nerve injury, a spinal cord injury, or a peripheral nerve injury.

In certain embodiments, treatment of the injured neuron results in at least one of the growth or regeneration of the injured neuron.

In certain embodiments, the injured neuron is an injured retinal ganglion cell, an injured corticospinal tract neuron, or an injured dorsal root ganglion neuron.

BRIEF DESCRIPTION OF TH DRAWINGS

The above and other objects and features of the present disclosure will become apparent from the following description of the disclosure, when taken in conjunction with the accompanying drawings.

FIG. 1 depicts data showing two FDA approved bioactive small molecules, glycopyrrolate and mexileline, enhance the intrinsic growth capacity axotomized dorsal root ganglion (DRG) neurons. Primary cultures of DRG neurons were prepared from adult C57BL/6 mice, and plated onto a poly-D-lysine and laminin-coated 8-well chamber. Glycopyrrolate and mexiletine were added into the cultured DRG neurons at various concentrations as indicated one hour after plating. 0.1% DMSO served as solvent control. The cultures were allowed to grow for 17 h. After fixation, the DRG neurons were immunostained with anti-βIII-tubulin primary antibodies highlighting the cell bodies of DRG neurons and their adjacent neurites for neurite outgrowth assay. (A) Average total neurite length was quantified using automated WIS-NeuroMath 5 software. Both glycopyrrolate and mexiletine induced robust neurite extension from axotomized DRG neurons compared with solvent controls. Scale bar: 500 μm. (B) Both glycopyrrolate and mexiletine did not exhibit any effects on cell survival. Mean±SEM of triplicates; * P<0.05, one-way ANOVA followed with Bonferroni post-hoc test.

Figure 2:
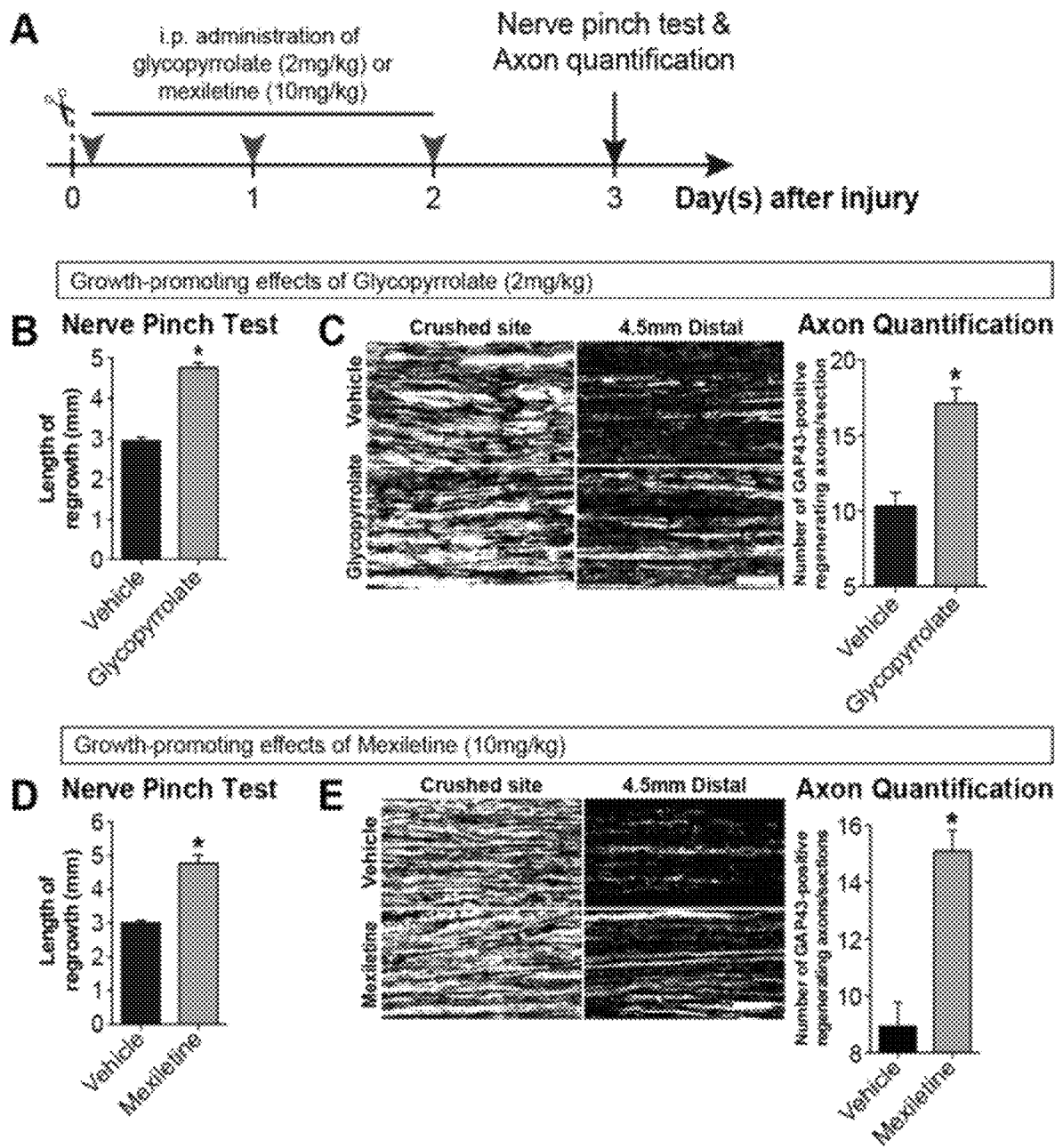

FIG. 2 depicts data demonstrating that glycopyrrolate and mexiletine promotes in vivo axon regeneration after peripheral nerve injuries. (A) Experimental paradigm for sciatic nerve pinch test. Sciatic nerve crush injury was performed on the left sciatic nerve of adult male C57BL/6 mice. We performed nerve pinch test in adult mice injected intraperitoneally with glycopyrrolate (2 mg/kg) or mexiletine (10 mg/kg) for 3 consecutive days after injury. (B-E) Both glycopyrrolate (B and C) and mexiletine (D and E) markedly accelerated in vivo axon regeneration after sciatic nerve crush injury as assessed by sciatic nerve pinch tests (n=5-6 per group). The most distal axonal regrowth in mice treated with glycopyrrolate and mexiletine was increased significantly by 61% and 59%, respectively. Number of GAP43-positive regenerating axons were increased by 73% in glycopyrrolate-treated mice and 67% in mexiletine-treated mice (n=3 per group). Scale bar: 100 μm. Mean±SEM; *P<0.05, Student's t-test.

Figure 3:
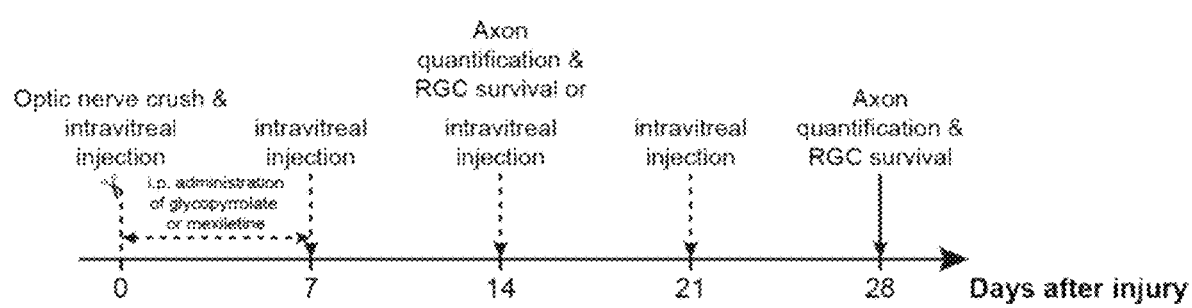

FIG. 3 depicts experimental paradigm to assess axon regeneration and retinal ganglion cell (RGC) survival after optic nerve crush injuries. Immediately alter optic nerve crush injury, adult male C57BL/6 mice (8-12 weeks old) were injected intravitreally with 1 μg of glycopyrrolate or mexiletine once per week for 2 weeks (i.e. days 0 and 7) or 4 weeks (i.e. days 0, 7, 14 and 21). Mice were also injected daily intraperitoneally with glycopyrrolate (2 mg/kg) or mexiletine (10 mg/kg) for 7 consecutive days after crush. Two days before tissue harvesting, mice were intravitreally injected with Alexa Fluor 555 conjugated cholera toxin subunit B (CTB-555) to trace regenerating axons, and optic nerves were treated with benzyl benzoate/benzyl alcohol (2:1) for tissue clearance. Serial transverse cryosections (20 μm) of retinae were immunostained with anti-RBPMS antibodies for RGC survival. RBPMS-positive RGCs were counted in every fifth section per retinae (3-5 sections). Axon quantification and RGC survival were performed on days 14 and 28 post-injury.

Figure 4:
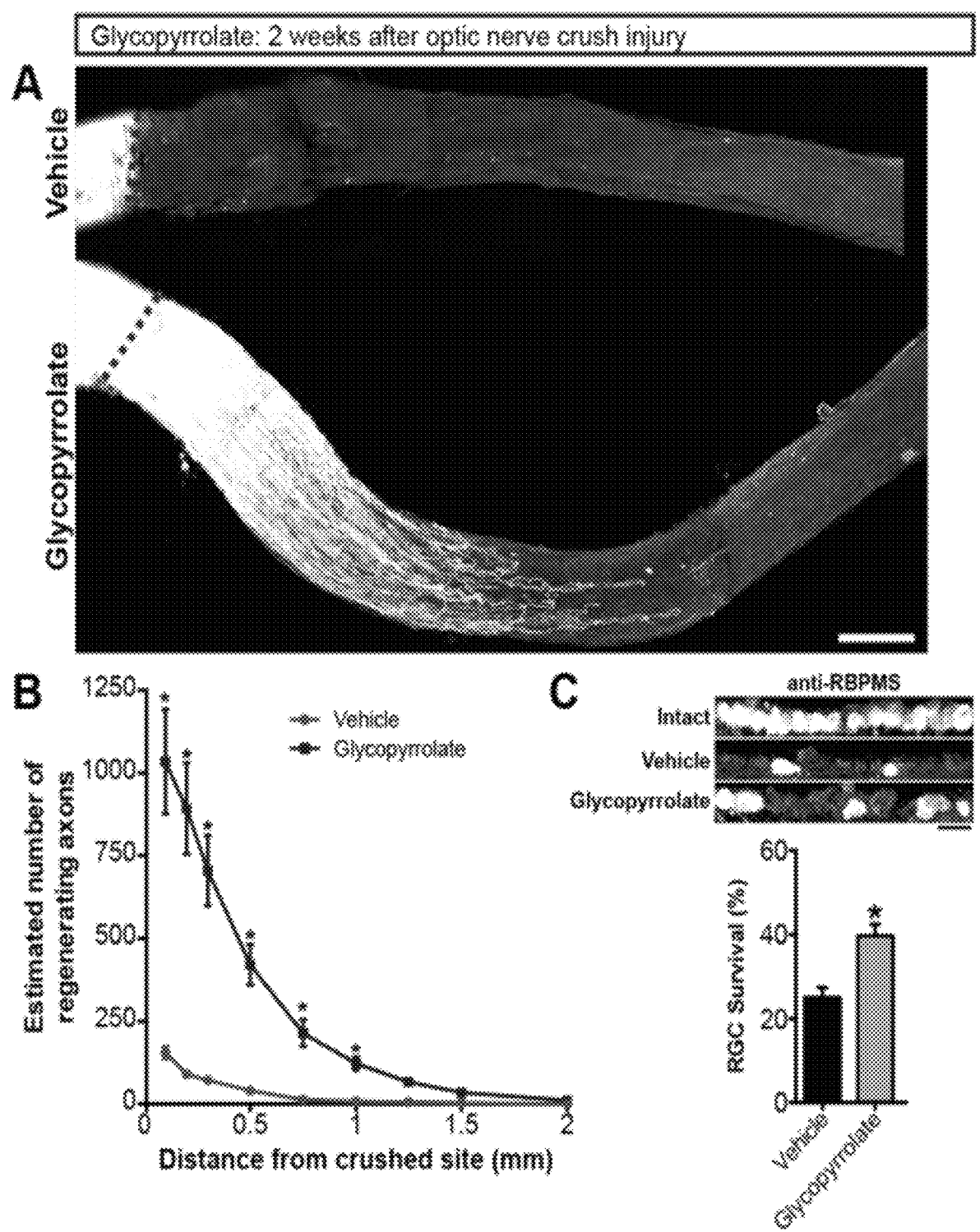

FIG. 4 depicts data demonstrating glycopyrrolate induces robust in vivo axon regeneration 14 days after optic nerve crush injuries. (A) At 2 weeks after injury, vehicle control groups (saline) showed no axons beyond the crush site, but we observed robust axon regeneration in glycopyrrolate-treated mice. Dotted line indicated the crushed site. (B) Glycopyrrolate induced more than 17-fold increase in the number of CTB-labelled regenerating axons extending 1.0 mm from the site of injury. (C) The RGC survival rate of glycopyrrolate treatment groups nearly doubled after injury, compared with vehicle control group 2-week post-injury. Scale bars: 200 μm in (A), 20 μm in (C). Mean±SEM (n=5-7 per group). *P<0.05, Student's t-test.

Figure 5:
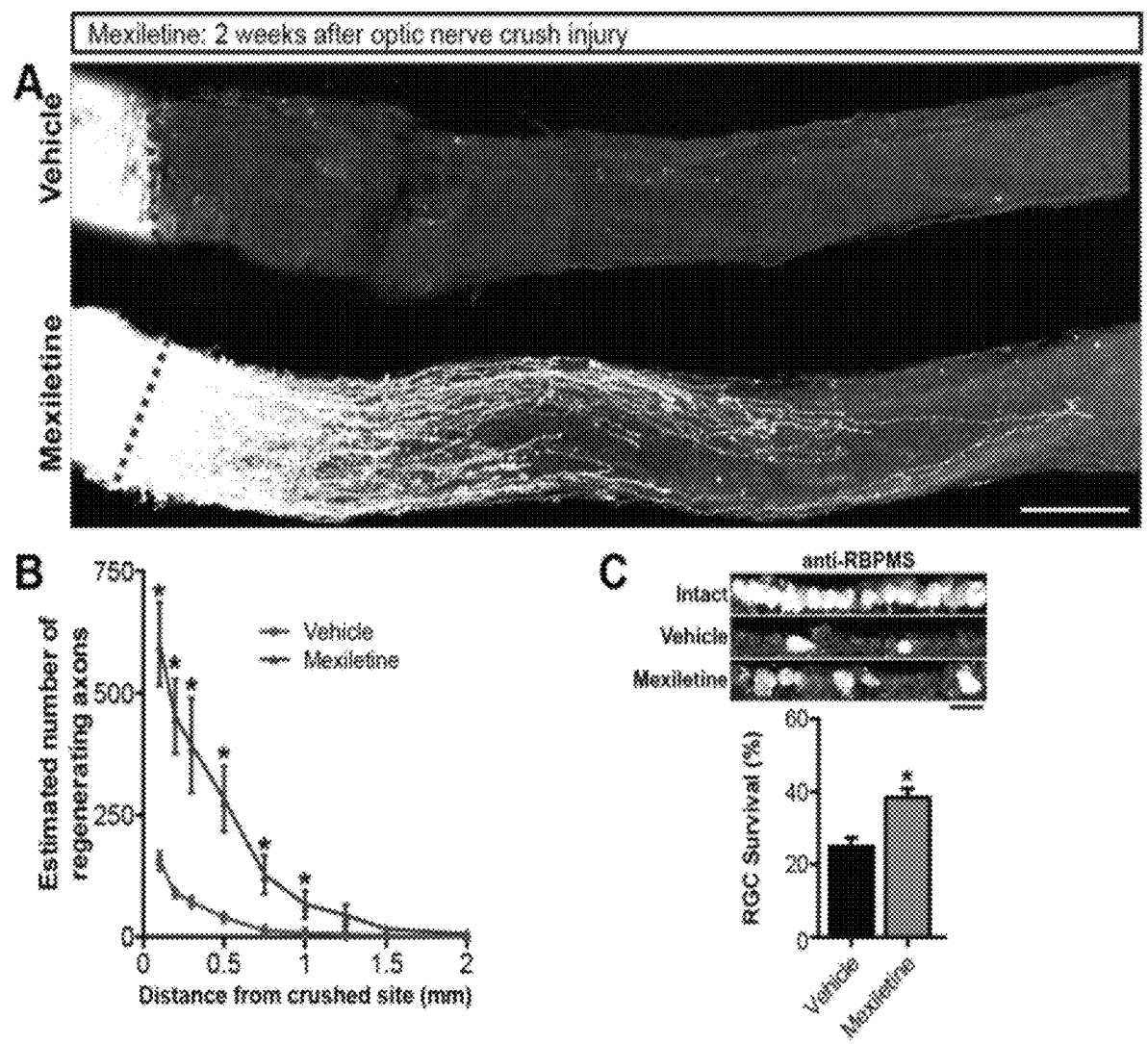

FIG. 5 depicts data demonstrating mexiletine promotes in vivo axonal regrowth 14 days after optic nerve crush injuries. (A and B) Mexiletine exhibited extensive axonal regrowth 2 weeks after injury at a level comparable to glycopyrrolate. (C) Similar to glycopyrrolate, mexiletine exhibited a strong protective effect on RGC survival 2 weeks after injury. Scale bars: 200 μm in (A), 20 μm in (C). Mean±SEM (n=5-7 per group). *P<0.05, Student's t-test.

Figure 6:
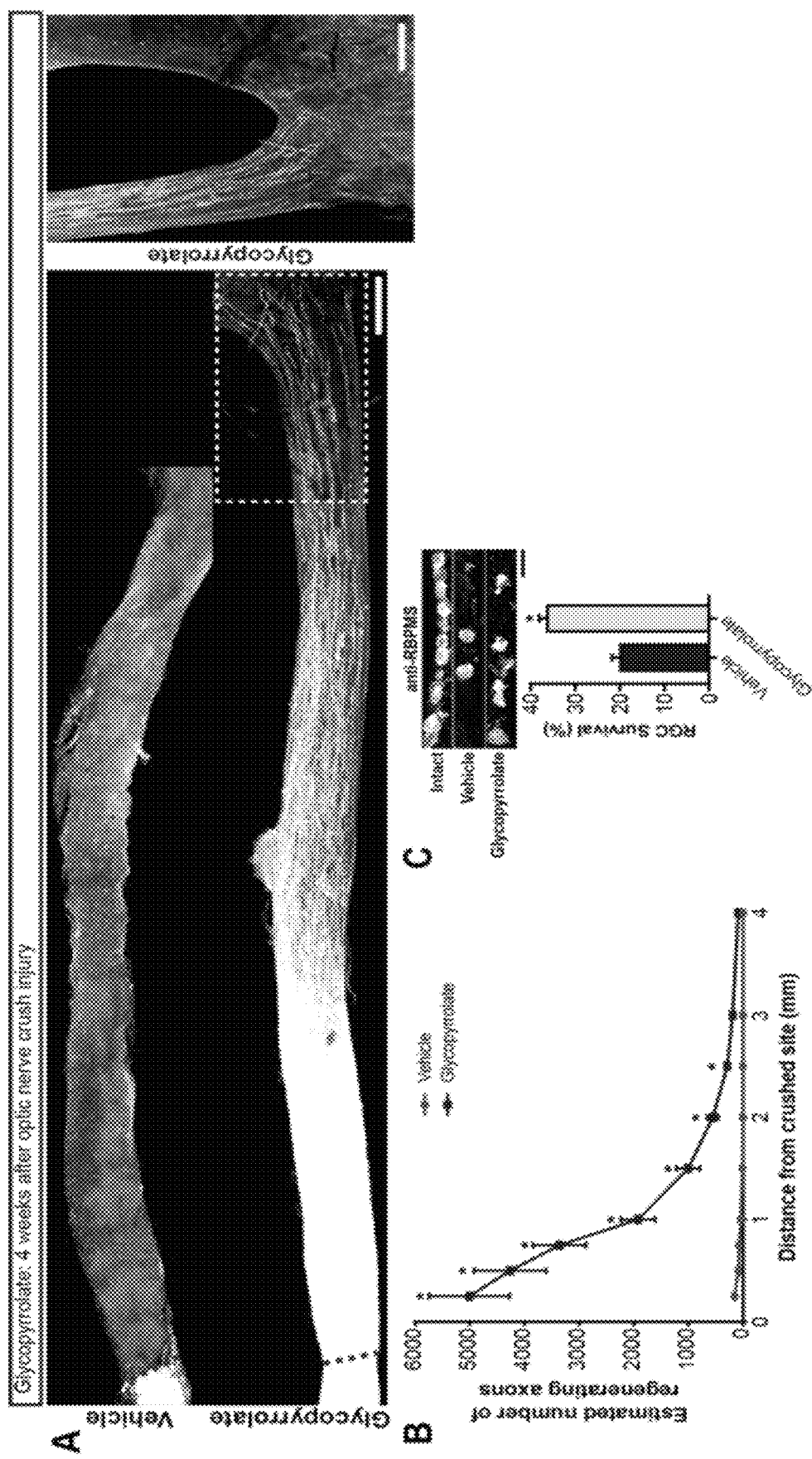
Figure 7:
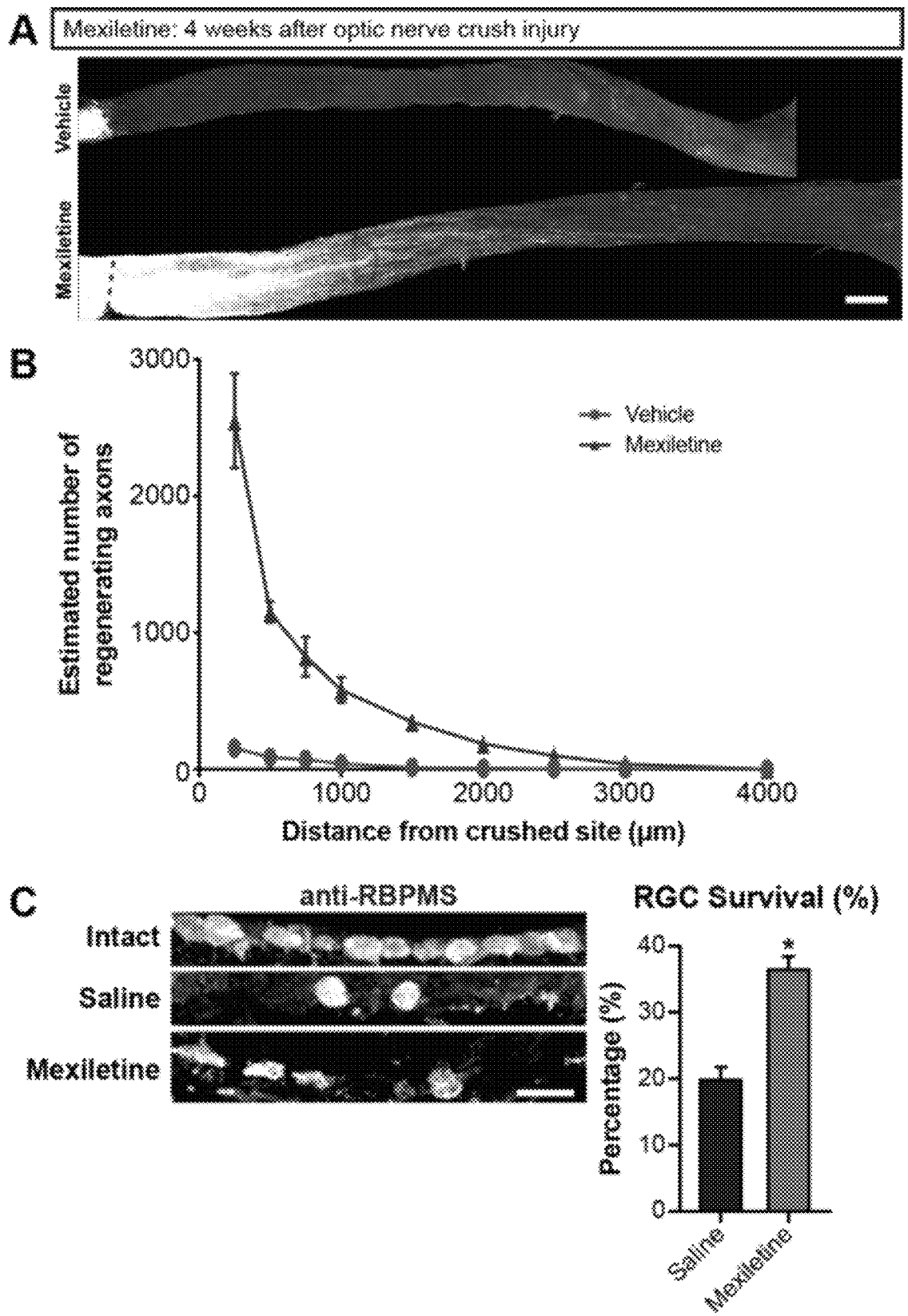

FIG. 6 depicts data demonstrating the regenerating axons can reach the optic chiasm in glycopyrrolate-treated mice 4 weeks after optic nerve crush injuries. (A) The promoting effect of glycopyrrolate became even more dramatic at 4 weeks after injury. Glycopyrrolate triggered intrinsic growth capacity of RGCs that enabled these cells to regenerate axons the entire length of the optic nerve and some of the regenerating axons reaching optic chiasm. High magnification depicting the area within the white box in the optic chiasm. Dotted line indicated the crushed site. (B) At 2 mm distal to the lesion site. glycopyrrolate treatment resulted in more than 70-fold increase in the number of CTB-labelled regenerating axons, compared with vehicle controls. (C) At 4 weeks after injury, glycopyrrolate induced a marked increase in RGC survival compared with vehicle-treated controls. Scale bars: 200 μm in (A), 20 μm in (C). Mean±SEM (n=5-7 per group). *P<0.05, Student's t-test FIG. 7 depicts data demonstrating mexiletine induces substantial axonal regrowth 4 weeks after optic nerve crush injuries. (A and B) Mexiletine-treated mice displayed substantial regrowth of RGC axons 4 weeks after injury. (C) Mexiletine induced a marked increase in RGC survival 4 weeks after injury compared with vehicle-treated controls. Scale bars: 200 μm (A), 20 μm in (C). Mean±SEM (n=5-7 per group). *P<0.05, Student's t-test.

DETAILED DESCRIPTION

Throughout the present disclosure, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the present disclosure and claims, unless the context requires otherwise, the word "include" or variations such as "includes" or "including", will be understood to imply the inclusion of a stated integer or group of integers, but not the exclusion of any other integer or group of integers.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

As used herein, the terms "treat", "treating", "treatment", and the like refer to reducing or ameliorating a disorder/disease and/or symptoms associated therewith. It will be appreciated, although not precluded, treating a disorder or condition does not require that the disorder, condition, or symptoms associated therewith be completely eliminated. In certain embodiments, treatment includes prevention of a disorder or condition, and/or symptoms associated therewith. The term "prevention" or "prevent" as used herein refers to any action that inhibits or at least delays the development of a disorder, condition, or symptoms associated therewith. Prevention can include primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

As used herein, the term "subject" refers to any animal (e.g., a mammal), including, but not limited to, humans, non-human primates, canines, felines, and rodents.

Where stereochemistry is not specifically indicated, all stereoisomers of the inventive compounds are included within the scope of the disclosure, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this disclosure.

The compounds described herein exist in particular stereoisomeric forms. The present disclosure contemplates all such compounds, including R- and S-enantiomers, and racemic mixtures thereof, as falling within the scope of the disclosure.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In certain embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The present disclosure provides method of treating a nervous system injury in a subject in need thereof, the method comprising: administering a therapeutically effective amount of a compound selected from the group consisting of glycopyrrolate (compound of Formula I), mexiletine (compound of Formula II), and a mixture thereof to the subject, wherein the compound of Formula I has the structure:

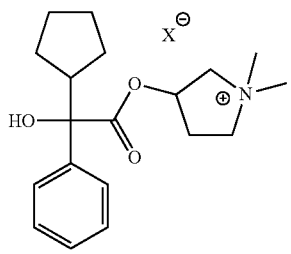

I or a solvate thereof, wherein X is a pharmaceutically acceptable anion; and the compound of Formula II has the structure:

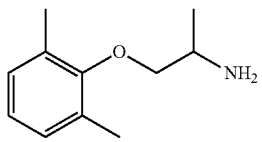

II or a pharmaceutically acceptable salt thereof or a solvate thereof.

The compound of Formula I comprises a pharmaceutically acceptable anion. The pharmaceutically acceptable anion may be any anion that has been previously used in a FDA-approved drug and/or is generally recognized as safe (GRAS). Pharmaceutically acceptable anions refer to relatively non-toxic, organic or inorganic anions including, but are not limited to, acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methyl sulfate, mucate, napsylate, nitrate, octanoate, oleate, pamoate, pantothenate, phosphate, polygalacturonate, propionate, salicylate, stearate, acetate, succinate, sulfate, tartrate, teoclate, tosylate, and the like. In certain embodiments, the pharmaceutically acceptable anion is chloride, bromide, sulfate, or tosylate. In certain embodiments, the pharmaceutically acceptable anion is bromide.

The compounds described herein comprise a stereogenic center. The compounds can exist in enantiomerically pure form or as a racemic mixture. In certain embodiments, the compounds described herein are substantially enantiomerically pure. Substantially enantiomerically pure forms of the compounds described herein have at least about 70% by weight of one enantiomer relative to the total weight of the preparation, such as at as at least about 75% by weight, such as at as at least about 80% by weight, such as at as at least about 85% by weight, such as at least about 90% by weight, and such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

The present disclosure also provides a pharmaceutical composition comprising a compound described herein and at least one pharmaceutically acceptable excipient and/or pharmaceutically acceptable carrier.

Accordingly, the present disclosure provides pharmaceutically acceptable compositions, which comprise a therapeutically-effective amount of the compound described herein, formulated together with one or more pharmaceutically acceptable carriers (additives) and/or diluents. The pharmaceutical compositions of the present disclosure may be specially formulated for administration in liquid form, including those adapted for the following: (1) parenteral administration a sterile solution or suspension.

As set out herein, certain embodiments of the compounds described herein may contain a basic functional group, such as amino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present disclosure. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the bromide, chloride, sulfate, bisulfate, carbonate, bicarbonate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the compounds of the present disclosure include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing the pharmaceutical comprising compounds include the step of bringing into association a compound described herein with the carrier and, optionally, one or more accessory ingredients. In general, the formulations are prepared by uniformly and intimately bringing into association a compounds described herein with liquid carriers (liquid formulation), liquid carriers followed by lyophilization (powder formulation for reconstitution with sterile water or the like), or finely divided solid carriers, or both, and then, if necessary, shaping or packaging the product.

Pharmaceutical compositions of the present disclosure suitable for parenteral administration comprise a compound described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate.

The pharmaceutical compositions may also contain adjuvants, such as preservatives, wetting agents, emulsifying agents and dispersing agents. Prevention of the action of microorganisms upon the compounds of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In certain embodiments, the pharmaceutical composition comprises a compound described herein at a concentration between about 0.1 µg/µl to about 20 µg/µl, 0.1 µg/µl to about 15 µg/µl, 0.1 µg/µl to about 10 µg/µl, 0.1 µg/µl to about 5 µg/µ1, 0.1 µg/µl to about 4 µg/µl, 0.1 µg/µl to about 2 µg/µl, 0.1 µg/µl to about 1.5 µg/µl, 0.5 µg/µl to about 1.5 µg/µl, 0.75 µg/µl to about 1.25 µg/µl, 0.9 µg/µl to about 1.11 µg/µl, or about 1 µg/µl.

In certain embodiments, the pharmaceutical composition comprises a saline solution comprising a compound described herein at a concentration between about 0.1 µg/µl to about 20 µg/µl, 0.1 µg/µl to about 15 µg/µl, 0.1 µg/µl to about 10 µg/µl, 0.1 µg/µl to about 5 µg/µ1, 0.1 µg/µl to about 4 µg/µ1, 0.1 µg/µl to about 2 µg/µ1, 0.1 µg/µl to about 1.5 µg/µl, 0.5 µg/µl to about 1.5 µg/µl, 0.75 µg/µl to about 1.25 µg/µl, 0.9 µg/µl to about 1.11 µg/µl, or about 1 µg/µl.

The nervous system injury can comprise an injury to the central nervous system or the peripheral nervous system.

The nervous system injury can be acute or chronic. A nervous system injury can comprise the complete severing or partial severing of a neuron, or crushing or compression injury to a neuron. In certain embodiments, the nervous system injury directly impairs the normal functioning of neuron(s). In certain embodiments, the nervous system injury indirectly impairs the normal functioning of the neuron(s). The nervous system injury can result from an acute or traumatic event, chronic event, pressure build-up, or chronic neurodegeneration. Injuries to a subject can result in injury to a neuron. Common causes of nervous system injury include, but are not limited to, disease and/or infection, ischemia, anoxia, hypoglycemia, contusion, laceration, trauma to the brain or spinal cord (such as caused by acute spinal cord damage or stroke), damage by exogenous chemical agents, and combinations thereof.

The nervous system injury can be the result of a disease, disorder, or condition in a subject, such as damage to retinal ganglion cells; traumatic brain injury; stroke related injury; a cerebral aneurism related injury: a spinal cord injury, including monoplegia, diplegia, paraplegia, hemiplegia and quadriplegia; a neuroproliferative disorder or neuropathic pain syndrome.

In embodiments, the subject that suffers from a neurological injury resulting from a trauma. The neurological injury may comprise injury to the optic nerve, the spinal cord, or a peripheral nerve injury.

In certain embodiments, the subject suffers from a disease or condition that results in nervous system injury. In certain embodiments, the disease or condition is selected from the group consisting of stroke, spinal cord injury, Huntington's disease, Parkinson's disease, Alzheimer's disease, multiple system atrophy, spino-cerebellar atrophy, motor neuropathy, epilepsy or seizures, peripheral neuropthy, cerebral palsy, glaucoma, age related loss of neurons or neuronal connectivity and related deterioration of sensory, motor, reflect, and cognitive abilities.

In certain embodiments, the subject that suffers from an injury caused by or associated with peripheral neuropathies, such as diabetic neuropathy, virus-associated neuropathy, botulism-related neuropathy; toxic polyneuropathy, nutritional neuropathy, angiopathic neuropathy, sarcoid-associated neuropathy; carcinomatous neuropathy; compression neuropathy, and/or hereditary neuropathy; and/or peripheral nerve damage associated with spinal cord injury.

Administration of a compound described herein to the subject can be by any one or combination of a variety of methods. The appropriate method(s) will depend upon the circumstances of the individual (e.g. the location of the nervous system injury or target neuron(s), the condition of the individual, the desired duration of the contact, whether local or systemic treatment is desired). The administration can be by any methods described herein that will result in contact of sufficient amount of a compound described herein to the target neuron to induce a therapeutic effect. For example, parenteral, enteral and topical administration can be used. The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. Enteral administration involves the esophagus, stomach, and small and large intestines (i.e., the gastrointestinal tract). The phrases "systemic administration," "administered systemically", "peripheral administration" and "administered peripherally" as used herein mean the administration of a compound other than directly into the central nervous system, such that it enters the animal's system and, thus, is subject to metabolism and other like processes, for example, subcutaneous administration. Administration may be topical (including ophthalmic), oral or pulmonary administration, e.g., by inhalation or insufflation, or intracranial, e.g., intrathecal or intraventricular, administration, topically to the eye, or by intraocular injection. In certain embodiments, the compound described herein is administered to the subject by any one or a combination of methods selected from the group consisting parenterally, enterally, and topically.

In certain embodiments, the compounds described herein are administered to the subject by any one or a combination of methods selected from the group consisting of intravitreally, intraperitoneally, suprachoroidally, subconjunctivally, retrobulbarly, intracamerally, and subretinally.

In certain embodiments, the compounds are administered to the eye. In instances in which the compound is administered to the eye, the route of administration can be selected from intravitreal injection, topical, intracameral injection, subconjunctival injection, sub-tenon injection, retro bulbar injection, sub-retinal injection, and peri-ocular or laterobulbar injection.

Specific routes of administration and the dosage regimen will be determined by skilled clinicians, based on factors such as the exact nature of the condition being treated, the severity of the condition, and the age and general physical condition of the patient.

The exact dosage amount of a compound described can vary according to factors known in the art including, but not limited to, the physical/chemical nature of the compound, the properties of the pharmaceutically acceptable carrier, the intended dosing regimen, the state of the subject's nervous system injury, and the method of administering the compound. Those of ordinary skill in the art, however, can readily determine the appropriate amount with consideration of such factors. A non-limiting range for the dosage of a compound described herein to the subject is about 0.1 mg/kg to about 100 mg/kg. In certain embodiments, the dosage is about 0.1 mg/kg to about 75 mg/kg, about 0.1 mg/kg to about 50 mg/kg, about 0.1 mg/kg to about 25 mg/kg, about 25 mg/kg to about 100 mg/kg, about 50 mg/kg to about 100 mg/kg, about 75 mg/kg to about 100 mg/kg, about 25 mg/kg to about 75 mg/kg, about 50 mg/kg to about 75 mg/kg, about 25 mg/kg to about 50 mg/kg, about 0.1 mg/kg to about 15 mg/kg, about 0.1 mg/kg to about 12 mg/kg, about 0.1 mg/kg to about 10 mg/kg, about 2 mg/kg to about 10 mg/kg, about 1 mg/kg to about 5 mg/kg, about 1 mg/kg to about 3 mg/kg, about 5 mg/kg to about 15 mg/kg, or about 8 mg/kg to about 12 mg/kg.

The present disclosure also provides a method of promoting growth, regrowth, and/or regeneration of a neuron, the method comprising contacting the neuron with a therapeutically effective amount of a compound described herein. Contacting the neuron can occur in vivo, in vitro or ex vivo. Neuron cells can be isolated from a subject and grown in vitro, using techniques well known in the art. The neuron may be a healthy neuron or an injured neuron. The neuron cell can be a central nervous system neuron or a peripheral nervous system neuron.

In certain embodiments, the method comprises: contacting the injured neuron with a compound selected from the group consisting of a compound of Formula I, a compound of Formula II, and a mixture thereof, wherein the compound of Formula I has the structure:

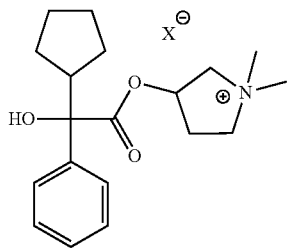

I or a solvate thereof, wherein X is a pharmaceutically acceptable anion; and the compound of Formula II has the structure:

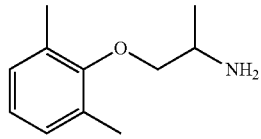

II or a pharmaceutically acceptable salt thereof or a solvate thereof, wherein the step of contacting the injured neuron occurs in vitro or ex vivo.

In certain embodiments, the neuron cell is an optic nerve neuron or a retinal neuron.

The optic nerve neuron can be an injured optic nerve neuron, and injury to the optic nerve neuron can be the result of branch and/or central vein/artery occlusion, trauma, edema, or glaucoma.

The retinal nerve neuron can be an injured retinal nerve neuron, and injury to the optic nerve neuron can be the result of macular degeneration, age related macular degeneration, retinitis pigmentosa, retinal detachments, or damage associated with laser therapy.

The neuron cell may be isolated from a subject that suffers from a disease or condition that results in nervous system injury. In certain embodiments, the disease or condition is selected from the group consisting of stroke, spinal cord injury, Huntington's disease, Parkinson's disease, Alzheimer's disease, multiple system atrophy, spino-cerebellar atrophy, motor neuropathy, epilepsy or seizures, peripheral neuropthy, cerebral palsy, glaucoma, age related loss of neurons or neuronal connectivity and related deterioration of sensory, motor, reflect, and cognitive abilities.

The neuron cell may be isolated from a subject that suffers from an injury caused by or associated with peripheral neuropathies, such as diabetic neuropathy, virus-associated neuropathy, botulism-related neuropathy; toxic polyneuropathy, nutritional neuropathy, angiopathic neuropathy, sarcoid-associated neuropathy; carcinomatous neuropathy; compression neuropathy, and/or hereditary neuropathy; and/or peripheral nerve damage associated with spinal cord injury.

The neuron cell may be isolated from a subject that suffers from a neurological injury resulting from a trauma. The neurological injury may comprise injury to the optic nerve, the spinal cord, or a peripheral nerve injury.

Glycopyrrolate and mexiletine can largely enhance the intrinsic growth capacity of cultured adult peripheral (i.e., dorsal root ganglion; DRG) neurons in vitro. Intraperitoneal injections of glycopyrrolate or mexiletine markedly promoted axonal regrowth in a mouse model of PNI. In CNS, direct intravitreal injections, in combination of intraperitoneal injections, of glycopyrrolate or mexiletine induced a robust axon regeneration after optic nerve crush injury in mice. The present disclosure establishes a novel role of glycopyrrolate and mexiletine for treatment of patients with nervous system injuries.

More particularly, glycopyrrolate and mexiletine are potent bioactive small molecules to be used to promote the intrinsic growth capacity of mature neurons. The use of glycopyrrolate and mexiletine in promoting the intrinsic growth capacity of neurons, a key factor for successful axon regeneration following injuries to our nervous system is reported herein.

Glycopyrrolate is a broad-spectrum antagonist of muscarinic acetylcholine receptor (mAChR), which shows no selectivity to M1-M3 mAChRs. It was originally used for treating sialorrhea in children patients with cerebral palsy to reduce drooling, and peptic ulcers in adult patients to reduce stomach acid secretion.

Mexiletine is a potent voltage-gated sodium channel blocker to inhibit the inward sodium current required for the initiation of nerve impulses, and therefore lowering the action potential. It is widely used as a class IB anti-arrhythmic drug to treat irregular heartbeat (arrhythmias). In a bioinformatics screening of FDA-approved small molecules, glycopyrrolate and mexiletine were identified as potential agents to promote axon regeneration after injury. The promoting effects of glycopyrrolate and mexiletine at various doses were investigated and the axonal outgrowth from axotomized DRG neurons in vitro was assessed. The data demonstrates that both glycopyrrolate and mexiletine can induce substantial neurite outgrowth from adult primary DRG neurons without exerting any neuronal survival effects (FIGS. 1A and B).

The therapeutic efficacy of glycopyrrolate and mexiletine in promoting axon regeneration after central and peripheral nerve injury was also determined. A sciatic nerve pinch test demonstrated that intraperitoneal injections of glycopyrrolate (2 mg/kg) or mexiletine (10 mg/kg) significantly enhanced axon regeneration 3 days after injury (FIGS. 4A and C). More GAP-43-positive regenerating axonal fiber were observed at 4 mm distal to the crushed site in mice treated with glycopyrrolate or mexiletine (FIGS. 4B and D). The therapeutic efficacy of both small molecules in promoting axonal regrowth after optic nerve crush injury was also demonstrated. While virtually no axonal regrowth was observed in untreated mice, both glycopyrrolate and mexiletine induced robust axon regeneration at 14 (FIG. 6A) and 28 days after injury (FIG. 7A). In addition, both glycopyrrolate and mexiletine markedly enhanced the survival of retinal ganglion cells (RGCs) (FIGS. 6B and 7B), further demonstrating their potency in promoting axon regeneration following nervous system injuries.

EXPERIMENTS

Assessing the Intrinsic Growth Capacity of Peripheral Neurons after Treating Glycopyrrolate and Mexiletine:

In the current study, the intrinsic growth capacity of peripheral neurons was first assessed, which is a critical determinant for successful axon regeneration after injury, after treating the neurons with glycopyrrolate and mexiletine. Primary culture of adult dorsal root ganglion (DRG) neurons is a widely used in vitro models to assess cues that could promote axonal outgrowth. Primary DRG neurons were prepared from adult C57BL/6 mice (8-12 weeks old). DRG neurons were dissected out, mildly digested with a solution of collagenase and dispase II (Roche Diagnostics), trypsinized and mechanically dissociated into single cell suspension using flame-polished Pasteur pipettes with three different diameters. Two thousand DRG neurons were plated onto an 8-well chamber slide pre-coated with poly-D-lysine and laminin (Sigma Aldrich), and cultured in full Neurobasal medium (Gibco) supplemented with B27, 200 mM L-glutamine, penicillin-streptomycin, 50 ng/ml NGF (Gibco), 10 µM Ara-C and 2 ng/ml GDNF (Gibco). Glycopyrrolate (5, 10 and 100 µM) or mexiletine (10, 50 and 100 µM) was added into the cultured neurons 1 hour after plating, and the cultures were allowed to grow for 17 hours.

After 17 hours of incubation, the cultures were fixed with 4% paraformaldehyde (PFA), blocked with 0.5% bovine serum albumin (BSA)/0.1% Triton X-100 in PBS for 1 hour at room temperature, and incubated with anti-β III-tubulin primary antibodies (1:800, Sigma Aldrich) for overnight at 4° C. After washing with PBS, the cultures were incubated with Alexa Fluor 488-conjugated secondary antibodies (1:300, Molecular Probes) for 1 hour at room temperature. To assess the neurite outgrowth of axtomized DRG neurons after treatment of glycopyrrolate or mexiletine, 30 non-overlapping images were taken at 10× magnifications using Nikon Ni-E microscope equipped with a motorized stage. Total neurite length of individual DRG neurons from each treatment condition were measured by automated WIS-NeuroMath software (Weizmann Institute of Science). The total neurite length of the neurons was averaged from at least 250 neurons per condition. Data was obtained from three separated experiments repeated in duplicate (FIG. 1).

Animal Model of Peripheral Nerve Injury:

In the current project, a sciatic nerve crush injury was used as an in vivo animal model for peripheral nerve injury. Adult male C57BL/6 mice (8-12 weeks old) were used for all experiments. All mouse husbandry and euthanasia were in compliance with the Institutional Animal Care and Use Committee (IACUC) guidelines. Surgical procedures performed were in accordance with protocols approved by the City University of Hong Kong Animal Research Ethics Sub-Committee and Department of Health, Hong Kong SAR. Under anesthesia, the left sciatic nerve was exposed, and crushed with 5/45 smooth forceps (Fine Science Tools) for 15 seconds at the level of external rotator muscles, distal to the sciatic notch after separation from the surrounding connective tissue (FIG. 2).

Treatment Paradigm of Glycopyrrolate and Mexiletine after Peripheral Nerve Injury:

Glycopyrrolate or mexiletine was first dissolved in 0.9% saline, and injected intraperitoneally immediately after sciatic nerve crush injury for 3 consecutive days at 2 mg/kg and 10 mg/kg, respectively (FIGS. 3A and B).

Assessment of the Extent of Axon Regeneration Following Peripheral Nerve Injury:

The extent of axon regeneration was evaluated using sciatic nerve pinch test, and verified by quantifications of GAP-43-positive regenerating axonal fibres 72 hours after sciatic nerve crush injury.

Sciatic Nerve Pinch Test:

Sciatic nerve pinch test was performed on the ipsilateral nerves 72 hours after sciatic nerve crush injury. The left sciatic nerve was first exposed to mid-thigh level under deep anaesthesia (i.e. 2.5% isoflurane). Under light anaesthesia (i.e. 1% isoflurane), a series of pinches were applied from the most distal part of the nerve (i.e. trifurcation), moving proximally towards the crushed site using smooth forceps (Fine Science Tools). The distance (in mm) representing the extent of axonal regrowth was recorded from the crushed site to the most distal point of the nerve where initial withdrawal response was observed after pinching (FIGS. 4A and C).

Quantification of Regenerating Axons:

After 72 hours of injury, the ipsilateral sciatic nerves were harvested to assess the extent of axon regeneration. After fixation with 4% PFA, the nerves were cut longitudinally into 12-µm-thick serial sections. The sectioned nerves were blocked with 0.5% BSA/0.1% Triton X-100 (Sigma Aldrich) in PBS for 1 hour at room temperature, and incubated with anti-GAP43 antibodies (marker for regenerating axons; 1:1,000, Millipore) for overnight at 4° C. After washing with PBS for 3 times, the cryosections were then incubated with Alexa Fluor 488-conjugated secondary antibodies (1:300, Molecular Probes) for 1 hour at room temperature. The whole sciatic nerves were imaged at 20× magnifications using Nikon Ni-E microscope equipped with a motorized stage, and stitched using NIS-Elements software. The average number of GAP-43-positive regenerating axonal fibres per section was determined at 4 mm distal to the crushed site from at least 3-5 sections (36-μm apart) in each animal (n=3 per group; 9-15 sections in total) (FIGS. 4B and D).

Animal Model of CNS Injury:

To further investigate the therapeutic potentials of glycopyrrolate and mexiletine in promoting axon regeneration after CNS injury, we used optic nerve crush injury, a well-established model for CNS regeneration, to assess the extent of axon regeneration after treating with glycopyrrolate or mexiletine. Adult male C57BL/6 mice (8-12 weeks old) were used in the entire study. The mice were first anesthetized with ketamine (100 mg/kg)/xylazine (10 mg/kg). The left optic nerve was exposed intraorbitally, and crushed with smooth forceps (Fine Science Tools) for 5 seconds at 1 mm distal to the optic disc (FIG. 5).

Treatment Paradigm of Glycopyrrolate and Mexiletine after Optic Nerve Injury:

Immediately after optic nerve crush injury, 1 μl of glycopyrrolate (1 μg/μl in 0.9% saline) or mexiletine (1 μg/μl in 0.9% saline) was intravitreally injected into the injured eye. A flame-polished micropipette was gently inserted into the periphery of the left eye, just behind the or a serrata, placed with an angle to prevent any damage to the lens. One microliter of glycopyrrolate or mexiletine solution was slowly infused at a constant flow rate of 200nl/min to avoid damage to the eyeball. The mice were received weekly intravitreal injections of glycopyrrolate or mexiletine. In parallel, glycopyrrolate (2 mg/kg) or/and mexiletine (10 mg/kg) was intraperitoneally injected to the mice at days 0 to 7 after injury. The mice were terminated for RGC survival and quantification of regenerating axons 14 days (FIG. 6) or 28 days after optic nerve injury (FIG. 7).

Quantification of Regenerating Axons and Retinal Ganglion Cell (RGC) Survival after Optic Nerve Injury:

Cholera toxin subunit B (CTB) was used to anterograde label the regenerating RGC axons. Three days before termination, 2 μg of CTB conjugated with Alexa Fluor 555 (CTB-555) was intravitreally injected to the vitreous of the injured eye using a micropipette inserted to the peripheral retinae. After fixing with 4% PFA, the whole optic nerves were incubated with increasing concentrations of ethanol (i.e. 50%, 80% and 95%) for 20 min at room temperature. The nerves were then incubated with 100% ethanol for overnight at 4° C. To remove any remaining droplet of water in the tissue, the nerves were incubated with 100% hexane for 3 hours at room temperature. The nerves were cleared with a solution of benzyl alcohol and benzyl benzoate at a ratio of 1:2. The cleared nerves were mounted on a microscope slide. Images were taken from the whole nerve at 20× magnifications using Carl Zeiss LSM 880 confocal microscope equipped with AiryScan Fast Mode and a motorized stage, with optical sections at 1.7 μm. The images were then stitched and maximum projected using ZEN2.3 Blue Software (Carl Zeiss).

To assess axon regeneration after treating with glycopyrrolate and mexiletine, the mean number of CTB-positive axons were determined by counting the number of CTB-positive axons extending across different nerve segments distal to the crushed site in 3-5 optical sections (10-μm-thick) from each mouse. The diameter of the nerve was measured at each point where the counting was performed. The estimated number of regenerating axons ($\Sigma a_d$) extending to the distance d, was calculated using the formula as shown below:

$$\Sigma a_d = \pi r^2 \times [\text{average axons}/mm]/t$$

t=thickness of the section (i.e. 10 μm)

To assess RGC survival after optic nerve crush injury, the eyeballs were frozen in OCT compounds after overnight fixation and cut into 20-μm-thick serial cryosections. The cryosections were blocked with 0.5% BSA/0.5% Triton X-100 for 1 hour at room temperature, and incubated with anti-RBPMS antibodies (1:500, Abcam) for overnight at 4° C. After washing with PBS for three times, the cryosections were incubated with Alexa Fluor 647-conjugated secondary antibodies (1:300, Molecular Probes) for 2 hours. Two to three images were taken from each section at 40 magnifications using Carl Zeiss LSM 880 confocal microscope equipped with AiryScan Fast Mode and a motorized stage. The RBPMS-positive RGCs were manually counted from every fifth sections from both ipsilateral (i.e., injured) and their respective contralateral (i.e. uninjured) retinae (i.e., 3-5 sections per retina), respectively, using ImageJ software with Cell Counter plugin. The percentage of RGC survival in ipsilateral retina was normalized with the average number of RBPMS-positive RGCs from contralateral retinae of the same mice.

Animal Model of Spinal Cord Injury (SCI):

T10 spinal cord hemisection will be performed on adult male C57BL/6 mice (8-12 weeks old). The mice were first anesthetized with ketamine (100 mg/kg)/xylazine (10 mg/kg). A laminectomy was performed at T12 vertebra in order to expose the spinal cord at T9 to T12. A T10 dorsal hemisection injury was performed by cutting the spinal cord with a pair of microscissors to a depth of 0.7 mm until the central canal. The muscle and skin were sutured, and the mice were placed on a heat pad at 37° C. until for recovery.

Treatment Paradigm of Glycopyrrolate and Mexiletine after SCI:

Immediately after SCI, 1 μl of glycopyrrolate (1 μg/μl in 0.9% saline) or mexiletine (1 μg/μl in 0.9% saline) was intrathecally injected into the injured spinal cord at lesion site. A flame-polished micropipette was gently inserted into the injured spinal cord. One microliter of glycopyrrolate or mexiletine was slowly infused at a constant flow rate of 200nl/min to avoid further damage to the spinal cord. The mice were received weekly intrathecal injections of glycopyrrolate or mexiletine. In parallel, glycopyrrolate (2 mg/kg) or mexiletine (10 mg/kg) was intraperitoneally injected to the mice at days 0 to 7 after injury.

Axonal Tracing of Regenerating CST and Dorsal Column Sensory Axons:

At 6 weeks post-SCI, the regenerating axons from CST were labeled by anterograde axonal tracing using BDA. A total of 0.8 μl of 10% BDA solution was injected intracranially into the sensorimotor cortex of the right hemisphere at the following co-ordinates relative to the bregma: anteroposterior (AP), −1.5 mm; mediolateral (ML), 0/−0.5/−1.0 mm; and dorsoventral (DV), −0.5 mm from the skull surface. A slow infusion rate of 150nl/min was maintained using an infusion pump (Harvard Apparatus) connected to a polished glass pipette to avoid any damages to the cortical area. To retrograde label the regenerating dorsal column sensory axons, 1 μl of CTB-555 (2 μg/μl) was directly injected into the left sciatic nerve 6 weeks after SCI using a polished glass pipette connected to an infusion pump (Harvard Apparatus).

Two weeks after the injections of axonal tracers, mice were perfused with 4% paraformaldehyde (PFA), and the spinal cord was harvested, post-fixed, cryoprotected in OCT compound, and cut into 25-μm-thick sagittal cryosections for axon quantifications. To visualize the BDA-labeled axons, 25-μm-thick sagittal spinal cord cryosections were blocked with 0.5% BSA/0.5% Triton X-100 (Sigma-Aldrich) for 1 hour, and incubated with streptavidin conjugated with Alexa Fluor 488 for 4 hours at room temperature. DAPI was used for counterstain to outline the injured area.

Regenerating CST and dorsal column sensory axons were quantified by the fluorescence intensity of BDA (for CST axons) and CTB (for dorsal column sensory axons), from every 4th sagittal spinal cord sections. Briefly, the lesion epicenter was identified by DAPI staining, and the fluorescence intensity of BDA or CTB was determined from every 250-μm-segment rostral (for CTB) or caudal (for BDA) to the lesion epicenter using ImageJ software (NIH). The fluorescence intensity of BDA or CTB at 250 μm caudal (for CTB) or rostral (for BDA) to the lesion epicenter was used for normalization to avoid any variations in tracing efficacy of each mouse. All analyses were performed blinded to treatments.

INDUSTRIAL APPLICABILITY

Both glycopyrrolate and mexiletine can promote the extent of axonal regrowth after peripheral nerve injury by enhancing the intrinsic growth capacity of mature neurons. They can be applied to treat patients with their PNS and CNS injured to promote axonal regrowth and subsequent functional restorations.

Intravitreal injections of glycopyrrolate or/and mexiletine at 1 μg/μl, combining with intraperitoneal injections of glycopyrrolate (2 mg/kg) or/and mexiletine (10 mg/kg) for 7 consecutive days, has extremely high potency to induce robust axon regeneration after optic nerve crush injury. At 1 month, some of the regenerating axons have successfully reached the optic chiasm in glycopyrrolate-treated mice. In untreated mice, axon regeneration virtually does not exist after optic nerve crush injury.

What is claimed is:

1. A method of treating a nervous system injury in a subject in need thereof, the method comprising: administering a therapeutically effective amount a compound of Formula I and optionally a compound of Formula II to the subject, wherein the compound of Formula I has the structure:

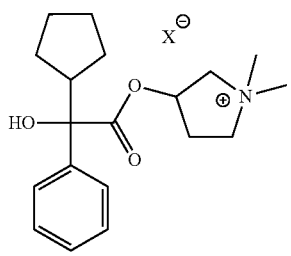

or a solvate thereof, wherein X is a pharmaceutically acceptable anion; and the compound of Formula II has the structure:

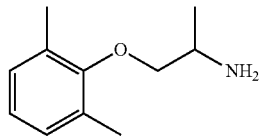

or a pharmaceutically acceptable salt thereof or a solvate thereof, wherein the compound of Formula I is administered to the subject by at least one route selected from the group consisting of intravitreally, intraperitoneally, suprachoroidally, subconjunctivally, retrobulbarly, intracamerally, and subretinally.

2. The method of claim 1, wherein X is bromide.

3. The method of claim 1, wherein the nervous system injury is selected from the group consisting of a central nervous system injury and a peripheral nervous system injury.

4. The method of claim 1, wherein treatment of the nervous system injury results in the regrowth of injured axons.

5. The method of claim 4, wherein the injured axons comprise neurons.

6. The method of claim 1, wherein the nervous system injury comprises a peripheral nerve injury.

7. The method of claim 1, wherein the nervous system injury comprises an optic nerve injury.

8. The method of claim 1, wherein the compound is administered to the subject by at least one route selected from the group consisting of intravitreally, intraperitoneally, and intrathecally.

9. The method of claim 6, wherein the compound is administered to the subject intraperitoneally.

10. The method of claim 7, wherein the compound is administered to the subject intravitreally and intraperitoneally at a dosage sufficient to induce axon regeneration in the subject.

11. The method of claim 1, wherein the compound is administered to the subject at a dosage of about 0.1 mg/kg to about 100 mg/kg.

12. The method of claim 1, wherein the compound is administered in a pharmaceutical composition comprising the compound at a concentration of about 0.1 μg/μl to about 20 μg/μl.

13. A method of treating an injured neuron, the method comprising contacting the injured neuron with a compound of Formula I and optionally a compound of Formula II, wherein the compound of Formula I has the structure:

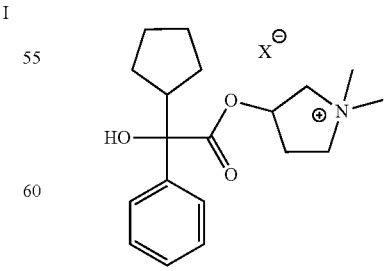

or a solvate thereof, wherein X is a pharmaceutically acceptable anion; and the compound of Formula II has the structure:

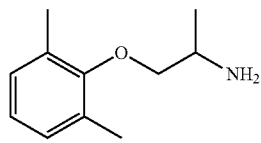

II or a pharmaceutically acceptable salt thereof or a solvate thereof, wherein the step of contacting the injured neuron occurs in vitro or ex vivo.

14. The method of claim 13, wherein the injured neuronal was injured as a result of an optic nerve injury, a spinal cord injury, or a peripheral nerve injury.

15. The method of claim 13, treatment of the injured neuron results in at least one of the growth or regeneration of the injured neuron.

16. The method of claim 13, wherein the injured neuron is an injured retinal ganglion cell, an injured corticospinal tract neuron, or an injured dorsal root ganglion neuron.

* * * * *